United States Patent [19]

Gottlieb

[11] Patent Number: 5,093,321

[45] Date of Patent: * Mar. 3, 1992

[54] DIALYSATES FOR TREATING AIDS AND ARC AND FOR OTHERWISE INCREASING IMMUNE RESPONSE

[75] Inventor: A. A. Gottlieb, New Orleans, La.

[73] Assignee: Imreg, Inc., New Orleans, La.

[*] Notice: The portion of the term of this patent subsequent to Aug. 28, 2001 has been disclaimed.

[21] Appl. No.: 469,353

[22] Filed: Jan. 24, 1990

Related U.S. Application Data

[63] Continuation-in-part of Ser. No. 183,905, Apr. 20, 1988, abandoned, which is a continuation-in-part of Ser. No. 902,683, Sep. 2, 1986, abandoned, which is a continuation-in-part of Ser. No. 643,724, Aug. 24, 1984, Pat. No. 4,616,079.

[51] Int. Cl.$^5$ .................. A61K 37/02; C07K 5/06; C07K 5/08

[52] U.S. Cl. ............................ 514/18; 530/331; 514/19

[58] Field of Search ............... 530/331; 514/19, 18, 514/17

[56] References Cited

U.S. PATENT DOCUMENTS 4,468,379 8/1984 Gottlieb ..................... 424/101
4,699,898 10/1987 Gottlieb ..................... 514/18

OTHER PUBLICATIONS

Fulton et al. *Chemical Abstracts* 1980, vol. 93, Abstract No. 24259n.

*Primary Examiner*—Lester I. Lee
*Attorney, Agent, or Firm*—Richard H. Stern

[57] ABSTRACT

Purified human leukocyte dialysates are described for treatment of AIDS, ARC, and other immunodeficient conditions. The dialysates are purified by HPLC processes, and are made available in a form that is free of endotoxin and pyrogen. A dialysate designated Beta-1.11 is found by amino acid sequencing to consist essentially of endogenous Tyr-Gly. A dialysate designated Beta-1.12 is found by amino acid sequencing to consist essentially of endogenous Tyr-Gly-Gly.

18 Claims, No Drawings

DIALYSATES FOR TREATING AIDS AND ARC AND FOR OTHERWISE INCREASING IMMUNE RESPONSE

This is a continuation-in-part based on the disclosure contained in U.S. patent application Ser. No. 183,905, filed 20 Apr. 1988, now abandoned, which priority date is claimed herein. That patent application was a continuation-in-part based on the disclosure contained in U.S. patent application Ser. No. 902,683, filed 2 Sept. 1986, and subsequently abandoned, which priority date is claimed herein. That application was a continuation-in-part based on allowed but then not yet issued U.S. patent application Ser. No. 643,724 (subsequently issued as U.S. Pat. No. 4,616,079), filed 24 Aug. 1984, and priority is claimed as to such date.

BACKGROUND OF THE INVENTION

1. Field of Invention

This invention concerns cell-mediated immunity and pathological conditions associated with a deficiency in cell-mediated immunity. Such conditions include, in particular, the Acquired Immune Deficiency Syndrome (AIDS), caused by the Human Immunodeficiency Virus (HIV), and AIDS-Related Complex (ARC). The invention also concerns other immunodeficient conditions.

A typical manifestation of cell-mediated immunity is the delayed type hypersensitivity ("DH") skin reaction. A DH skin reaction is observed when an appropriate antigen is injected subcutaneously. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings—specifically, perivascular infiltration of leukocytes and monocytes in the inflamed area. The cells seen at the site of a DH reaction are derived from the peripheral blood leukocyte population.

The mechanisms of cell-mediated immunity are as yet incompletely understood. It is known that the cells which mediate the response are capable of responding in a variety of ways to a challenge from an antigen. These responses include: proliferation of cells bearing specific sensitivity to a given antigen; the induction and multiplication of cells mediating a variety of immune functions, including antibody production; and reactions against foreign cells and tumors.

The present invention relates to the discovery of purified human leukocyte dialysates containing endogenous amplifiers of the immune system, which are isolated from dialyzed extracts of leukocytes. These amplifiers profoundly affect the quality and quantity of cell-mediated immunity responses; and are useful in the treatment of AIDS, ARC, and other clinical conditions characterized by inadequate reaction to antigens.

OTHER BACKGROUND

Earlier Gottlieb patents

In Gottlieb U.S. Pat. No. 4,468,379, it was disclosed that endogenous materials exist that amplify the speed and magnitude of cell-mediated immune system response. These amplifier materials are distinguished from so-called transfer factors in that amplifiers do not transfer to a subject an immune response to a mitogen or antigen to which the subject has not previously been exposed and is not concurrently exposed, while transfer factors are said to do so. Moreover, amplifiers non-specifically increase cell-mediated immune system responses to mitogens and antigens to which the subject has previously been or concurrently is exposed, while transfer factors are specific to particular antigens.

The material designated "amplifier 1" in the '379 patent is now known by the inventor to be a mixture of various things. They include: what are referred to subsequently in the present patent application as YG-material and YGG-material, another as-yet undefined amplifier, various amino acid products, and other materials.

The foregoing materials (and in particular the constituent amplifiers) occurred in amplifier 1 as a mixture in varying proportions, depending on the identity of the blood sample from which the source of amplifier 1 was derived. The reason for that is that the content of a human blood sample varies from donor to donor and even for the same donor from time to time, depending on the state of the immune system of the donor. The fact that the content of amplifier 1 varied from sample to sample adversely affects the repeatability of experiments directed toward establishing the immunological activity of amplifier 1. That in turn adversely affects one's ability to establish product identity, standard dosages, therapeutic regimens, assays, and the like for amplifier 1.

It was suggested in Gottlieb U.S. Pat. No. 4,616,079 (a parent of this application) that amplifiers appear to act on T-helper cells (T4 cells) in a way that causes them to produce chemical mediators (lymphokines) whose effect is to increase the speed and/or magnitude of cell-mediated immune system response to antigens and other means of activating a cell-mediated immune system response. Indicia of this immune system response include DH reaction to recall antigens, production of IL-2 and gamma interferon, and potentiation of cytotoxic cells.

It is known that various diseases and pathological conditions, such as Acquired Immune Deficiency Syndrome (AIDS) and AIDS-Related Complex (ARC), as well as chemotherapy, radiation, and ageing, depress the immune system response. As a result, there is increased susceptibility to opportunistic infections, malignancies, and other pathological conditions that a normal immune system would have confronted. Frequently (and for some conditions, invariably), the result is death. Administration of amplifiers provides a means of improving cell-mediated immune system responsiveness, where the cell-mediated immune system remains sufficiently intact for it to respond to such administration.

Earlier Gottlieb patents describe means of extracting amplifier materials from human leukocyte dialysates by reverse-phase HPLC processes. However, until recently the inventor did not have sufficiently detailed information about the molecular structure of the constituents of such purified dialysate fractions to permit identification of the structures of their immunologically active components. In large part this was because a way had not yet been discovered to purify the dialysates sufficiently to permit necessary analysis. In an application filed during the pendency of the parent applications of the instant application, and now issued as Gottlieb U.S. Pat. No. 4,699,898, as well as in other related patent applications of the inventor, the inventor disclosed his discovery of peptide products containing Tyr-Gly and Tyr-Gly-Gly amino acid residue sequences, that are immunologically active components in the partially purified dialysate fractions previously described in earlier Gottlieb patents, such as Gottlieb U.S. Pat. No. 4,616,079 (a parent of this application).

The earlier Gottlieb patents may also be consulted for other general background information on amplifiers and their use. In this regard, mention should also be made of Gottlieb EPO pat. app. pub. no. 0173889 (12.03.86), which is based on both Gottlieb U.S. Pat. No. 4,699,898 and a parent application of the instant application.

Plotnikoff

Plotnikoff U.S. Pat. No. 4,537,878 discloses and claims the use of endogenous endorphins and enkephalins to stimulate the immune system. The dosage amounts actually used in vivo (Plotnikoff's Examples VIII to XI) were from 1 microgram (ug) per kg to 50 ug/kg, single i.v. dose. Elsewhere, however, Plotnikoff refers to a therapeutic dose of from 1 ug/kg to 30 mg/kg, and to a preferable dosage rate of from 0.01 fg/kg to 250 ug/kg. No explanation is given for the inconsistencies, and no data in the specification indicates a reason why these latter dosage rates were mentioned or claimed. (They do not appear in Examples or similar data.)

The molecular species whose use Plotnikoff discloses are the endogenous enkephalin pentapeptides Tyr-Gly-Gly-Phe-Leu and Tyr-Gly-Gly-Phe-Met, and longer endorphin polypeptide extensions thereof (extended from the C-terminal end). Plotnikoff does not disclose use of any nonendogenous peptides, nor anything concerning use of dipeptides, tripeptides, or tetrapeptides. Plotnikoff does not indicate that Tyr-Gly or Tyr-Gly-Gly have any immunological or other utility. Plotnikoff does not show that any products have utility in treating AIDS or ARC.

Schwartz

Schwartz et al., Biological inactivation of enkephalins and the role of enkephalin-dipeptidyl-carboxypeptidase ("enkephalinase") as neuropeptidase, 29 Enkephalin Metabolism 1715 (1981), extensively reviews work that various investigators have done in the field of enzymatic breakdown of enkephalins. Schwartz summarizes the paper as follows:

> In this review it will be shown that enkephalins are rapidly hydrolyzed in vivo and that several peptidase activities have been identified which are able to cleave these molecules to give various biologically-inactive fragments.

Schwartz et al. and the work summarized in the review teach that various endogenous enzymes cleave (hydrolyze) the Gly-Phe, Gly-Gly, and Tyr-Gly bonds of endogenous mammalian polypeptides, such as Leu-enkephalin (Tyr-Gly-Gly-Phe-Leu) and Met-enkephalin (Tyr-Gly-Gly-Phe-Met), into what Schwartz alleges are "biologically inactive fragments." Such fragments include what Schwartz refers to as Tyr-Gly, which in context apparently means a dipeptide containing Tyr and Gly amino acid residues, in that order. But Schwartz does not indicate what side chains or other groups, if any, are attached to the amino acid residues or what specific molecular structure is present in the Tyr-Gly product.

Schwartz makes a statement in this paper, at FIG. 2, p. 1722 thereof, indicating that he has isolated Tyr-Gly-Gly by a TLC (thin-layer chromatography) process, after incubation in the presence of puromycin, an aminopeptidase inhibitor, citing Schwartz et al., 22 Adv. Biochem. Psychopharmac. 219-315 (1980). (Schwartz does not make any similar statement about Tyr-Gly.) Schwartz does not disclose any such process, however, nor does any of the contemporary or earlier literature of which the present inventor is aware. The inventor considers that Schwartz does not teach how to isolate an endogenous Tyr-Gly-Gly product, and that persons of ordinary skill in this art would not be able to devise such a process by reading the Schwartz papers. Moreover, the inventor is not aware of any TLC process by which endogenous Tyr-Gly or Tyr-Gly-Gly can be isolated in a substantially pure form, free of pyrogen, endotoxin, and similar substances.

Schwartz does not mention any immunological activity or other utility of what he characterizes as useless and biologically inactive fragments resulting from enzymatic action on enkephalins.

Commercial Tyr-Gly

Tyr-Gly is sold as a chemical reagent (L-tyrosylglycine) by Sigma Chemical Co., St. Louis, Mo., among others. Tyr-Gly is not sold in U.S.P. grade, and it is illegal under applicable laws to sell Tyr-Gly for use as a pharmaceutical. Commercial grade Tyr-Gly is not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations. To the extent of the inventor's knowledge, no pharmaceutical preparations of this product are or have been available and no medicinal use of this product has been described by a prior inventor.

Commercial Tyr-Gly-Gly

Tyr-Gly-Gly is sold as a chemical reagent (L-tyrosylglycylglycine) by Sigma Chemical Co., St. Louis, Mo, among others. Tyr-Gly-Gly is not sold in U.S.P. grade, and it is illegal under applicable laws to sell Tyr-Gly-Gly for use as a pharmaceutical. Commercial grade Tyr-Gly-Gly is not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations. To the extent of the inventor's knowledge, no pharmaceutical preparations of this product are or have been available and no medicinal use of this product has been described by a prior inventor.

SPECIAL TERMINOLOGY

YG means Tyr-Gly (also known as L-tyrosylglycine). YGG means Tyr-Gly-Gly (also known as L-tyrosylglycylglycine).

YG-material means a member of a group consisting of a set of molecular species wherein each molecule contains a Tyr-Gly amino acid residue sequence, and no other amino acid residues. The molecule may be in the form of a simple Tyr-Gly sequence, or the molecule may be methylated, amidified, esterified, acetylated, etc. YG-material does not include tripeptides or higher polypeptides. However, two YG-materials (e.g., two molecules of Tyr-Gly) may be complexed together in the form: (Tyr-Gly)Zn+ +(Tyr-Gly), or they may be dimerized as in the form:

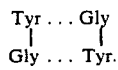

Such a complex or dimer is not considered a tetrapeptide, but merely two dipeptides complexed together or dimerized.

YGG-material means a member of a group consisting of a set of molecular species wherein each molecule contains a Tyr-Gly-Gly amino acid residue sequence, and no other amino acid residues. The molecule may be in the form of a simple Tyr-Gly-Gly sequence, or the molecule may be methylated, amidified, esterified, acetylated, etc. YGG-material does not include dipeptides, tetrapeptides, or higher polypeptides. However, two YGG-materials (e.g., two molecules of Tyr-Gly-Gly), or YG-material and YGG-material, may be complexed together or dimerized. Such a complex or dimer is not considered a pentapeptide or hexapeptide.

Endogenous YG-material means YG-material produced within the body. Endogenous YGG-material means YGG-material produced within the body.

Extraneous-peptide amino acid residue sequences means any and all amino acid residue sequences except Tyr-Gly and Tyr-Gly-Gly. As used herein, "sequence" refers to a plurality of residues, and the term excludes a molecule with only a single amino acid residue, such as glycine.

The abbreviations u, n, p, and f refer, respectively, to micro, nano, pico, and femto. The abbreviation M means moles or Molar, as the context indicates; thus, fM may mean femtomoles or femtoMolar, depending on context.

The term "fg/kg," used in connection with a dosage amount for a person, means femtograms of dosage material per kilogram of the person's bodyweight. Similarly, "moles/kg" means moles of dosage material per kilogram of the person's bodyweight; "fM/kg" means femtomoles per kilogram of the person's bodyweight.

SUMMARY OF THE PRESENT INVENTION

The inventor has discovered that administration to AIDS and ARC patients of endogenous materials containing the amino acid residue sequence YG can alleviate certain symptoms of AIDS and ARC, can reverse certain pathological effects associated with AIDS and ARC, and appears to improve the clinical condition of some AIDS and ARC patients. Such treatment does not cure AIDS and ARC, but it is therapeutically useful in slowing the normal progression of AIDS and ARC. In particular, the treatment significantly delays the normal progression to AIDS that occurs in ARC patients.

The inventor has also discovered more general immunological utility for the foregoing endogenous materials and related synthetic materials. The materials of the invention are amplifiers of the immune system (as that term is used in Gottlieb U.S. Pat. No. 4,616,079). Thus they may be used for the therapeutic purposes described in the above-cited Gottlieb patents.

Generally speaking, the endogenous products of this invention are the reult of the inventor's discovery of processes leading to the extraction of highly purified forms of amplifier materials from leukocyte dialysates. The instant products are more free of extraneous material than any earlier amplifier products were.

Further, the elimination of extraneous material and the fractionation of mixtures of molecular species into the constituent species has resulted in achieving greater potency (in terms of weight of dosage amount) and greater repeatability in the resulting products than was possessed by the initial materials or previously discovered amplifier materials, such as "amplifier 1," described above. Each of those features is considered medically significant.

DETAILED DESCRIPTION OF THE PREFERRED EMBODIMENTS

Section I of the specification describes high-pressure liquid chromatography (HPLC) processes for purification of endogenous amplifier materials derived from human leukocyte dialysates. Section II describes human biological assays of the immunological activity of such materials. Section III describes human therapeutic use of such materials, including treatment of actual AIDS and ARC patients. Section IV describes various other tests and assays.

I. Reverse Phase Liquid Chromatography Processes

Processes are now described by which endogenous amplifier materials are extracted from human leukocyte dialysates. The procedures and reagents used herein were chosen to provide sterile and non-toxic products for human treatment. The HPLC equipment used is that described in Gottlieb U.S. Pat. No. 4,616,079, cols. 5-6.

EXAMPLE 1

Extraction of Beta

Leukocyte pellets were prepared in accordance with Example 1 of Gottlieb U.S. Pat. No. 4,616,079 and set aside.

An aqueous potassium phosphate solution was prepared by adding 5M KOH aqueous solution dropwise to 0.02M reagent grade phosphoric acid aqueous solution until the pH of the solution was adjusted to pH 5.0. The solution was delivered to a Perkin-Elmer HPLC machine, along with HPLC grade acetonitrile. The machine was programmed to deliver the following input solvent gradients: (1) 10 minutes of 0.1% concentration of acetonitrile in phosphate solution, constant gradient; and (2) 45 minutes of 0.1% to 10.0%, linear gradient. The flow rate was set at 1 ml/min.

Then, the leukocyte pellets were reconstituted and 5-10 mg of the material was loaded into a "MU BONDAPAK" octadecylsilane (O.S.) resin column. HPLC was commenced.

As effluent was collected, the ultraviolet absorption of the effluent was scanned with the machine's ultraviolet detector (210 nm, full scale=0.32 units). A plot of the absorption data of this process is shown in FIG. 1 of Gottlieb U.S. Pat. No. 4,616,079. Apparent solvent concentrations, retention times, and ultraviolet absorption were recorded. The results of the run are summarized below:

Alpha. A distinct doublet ultraviolet absorption peak was observed at retention time 12-14 minutes (approximately 0.5 to 0.9% acetonitrile concentration as observed on the machine's display and approximately 0.1 to 0.2% estimated actual concentration). The material accompanying this peak is designated herein as Alpha. It has no known immunological activity. But its elution serves as an indication ("marker") that material designated herein as Beta, which has been discovered to have amplifier activity, is about to elute.

Beta. Beta eluted approximately 3 minutes later, between approximately 15 and 20 minutes retention time. It was accompanied by a sharp, single ultraviolet absorption peak (hereinafter referred to as the Beta peak) reaching full scale. Displayed solvent concentration was 1.2 to 2.2%; estimated solvent concentration was 0.4 to 1.5%.

Frequently, in runs of this process, the material at the front edge of the Beta peak contained a material hereinafter described as Beta 1.12 and identified as endogenous YGG-material. Sometimes, such material appeared as a shoulder on the Beta peak. (As described below, Beta material can be fractionated further.)

Gamma. Immediately after Beta, at retention time between approximately 17 and 22 minutes, material designated herein as Gamma eluted. The Gamma material was characterized by either a distinct broad peak of ultraviolet absorption or as a shoulder on the absorption indication at the end of the elution of Beta. Gamma is without known immunological activity.

Delta. A group of peaks were then observed in the retention time range of from 23 to 36 minutes. The first of these peaks (a rather low one, less than 30 or 40% of full scale) corresponded to (i.e., occurred with the elution of) biologic material designated herein as Delta, which has been discovered to have amplifier activity. Delta eluted in the retention time range of approximately 26-28 minutes. Solvent concentration indicated on the visual display of the machine was from 3.5 to 4.0%, while estimated actual solvent concentration was 2.8 to 3.3%. Delta did not maintain a well-fixed location in this process, and sometimes either did not come off the column at all or was buried in the next material (Epsilon).

Epsilon. The next large absorption peak in the group was approximately 20% (or much more) of full scale, occurred about a minute later at retention time 27-30 minutes, and was a broad single peak or a doublet; the peak accompanied material designated herein as Epsilon. Epsilon is without known immunological activity.

Zeta. The absorption peak immediately following, approximately 2 minutes later, at retention time about 29-32 minutes, is designated herein as Zeta. Zeta has been discovered to have amplifier activity. Zeta can by a further process be separated into two moieties, Zeta-1 and Zeta-2, the second of which is has been discovered to contain the entire amplifier activity of this material.

Other materials, not discussed herein, but discussed in Gottlieb U.S. Pat. No. 4,616,079, eluted thereafter in this process.

The materials of Example 1 are contaminated with phosphate ions, are imperfectly purified from extraneous material (material having no known useful immunological activity), and are considered unsuitable for administration to human subjects. A further HPLC procedure with a different solvent system has been discovered to remove phosphate and extraneous material from the products of Example 1. The resulting material appears to be considerably more free of extraneous material and was considered suitable for administration to human subjects (as discusssed below).

EXAMPLE 2

Beta-1.0 Process

The material of preceding Example 1 was further purified and separated by HPLC on the analytic column. First, a 0.1% (v/v) aqueous trifluoroacetic acid (Mallinckrodt, Inc., Paris, Ky.) solution was prepared, and the pH of the solution was adjusted to pH 2.5 by the dropwise addition of sufficient 5M KOH aqueous solution. The solution was delivered to the Perkin Elmer machine, along with HPLC grade acetonitrile.

The machine was programmed for a 45 minute linear gradient of 0.1% to 45% concentration of acetonitrile in the trifluoracetic acid solution. (A 25-minute run to 25% is acceptable, but 45 minutes to 45% is more conservative.) The flow rate was set at 1 ml/min.

Beta fractions from approximately 4 procedures of Example 1 were pooled and loaded as starter material into a "MU BONDAPAK" brand of O.S. column; and HPLC was commenced. The effluents were scanned with the ultraviolet absorption detector, as in the preceding example. Full scale was set at 1.28 absorption units.

Contaminating Gamma material eluted at 8-11 minutes and was discarded. Displayed solvent concentration range was 8-11%, estimated actual solvent concentration was 4.8-7.8%. The absorption peak associated with Gamma was approximately 30-40% of full scale.

Material hereinafter designated as Beta-1.0 eluted at 15-18 minutes. Displayed solvent concentration range was 15-18%; estimated actual solvent concentration was 11.8-14.8%. The absorption peak was at least full scale and was quite sharp.

Analysis of Beta-1.0 indicates the presence of a mixture of molecular species. Two have been found to have intrinsic amplifier activity and are further discussed hereinafter. These two are a dipeptide material consisting essentially of a YG sequence, and a tripeptide material consisting essentially of a YGG sequence. The relative amounts of YG-material and YGG-material vary from sample to sample, approximately in the range 25:1 to 10:1, as is to be expected with human-derived immunologically active products. The average ratio of YG-material:YGG-material is between 16:1 and 20:1.

In addition, a third intrinsically active amplifier has been found present, which apparently consists of a nonpeptide, and is present in approximately the same relative amount as YGG-material. In addition, dried Beta-1.0 contains approximately 90% phenylalanine plus small amounts (less than 5% (w/w)) of other materials, notably Phe-Ser, Gly-Gly, and Gly-Glu; all of these materials were tested and found to lack intrinsic amplifier activity. Extensive clinical work with Beta-1.0 is described hereinafter. The terms "Beta-1.0" and "IMREG-1" are interchangeable. The term IMREG-1 is a registered trademark of Imreg Inc. and has been used to designate Imreg Inc.'s Beta-1.0 preparation that has been used in clinical tests of AIDS and ARC patients described below.

It has been found that Beta-1.0 is a constituent of the product designated "amplifier 1" in Gottlieb U.S. Pat. No. 4,468,379. Amplifier 1 also contains another amplifier, whose identity the inventor has not determined, and other substances. The two amplifiers are present in proportions that vary from sample to sample.

EXAMPLE 3

Amplifier 1 Fractionation

The procedure of Example 2 is repeated using amplifier 1 of U.S. Pat. No. 4,468,379 as starting material. The procedure is repeated with five different samples of amplifier 1, each derived from approximately $10^{10}$ leukocytes, and prepared over a period of six months from available leukocyte sources.

Varying quantities of Beta-1.0 are derived from the different samples, the yield being from approximately 20% to 60% depending on which sample is utilized. The remaining non-Beta-1.0 material is also collected and is found also to possess amplifier activity, as measured by DH skin test assay.

The inventor found the Beta-1.0 product of Example 2 to contain a considerable amount of phenylalanine, and other amino acid products, many of which were found to lack any intrinsic immunological activity. It was not feasible to ascertain the molecular structure of the intrinsically immunologically active material of Beta-1.0, because of the other material present. The inventor therefore developed a different HPLC system to permit such a determination.

EXAMPLE 4

Ethanol/Beta-1.1 Process

The Beta material developed from the pH 5 phosphate gradient of Example 1 was dried in a vacuum evaporator without heat. The material was reconstituted in 0.1% trifluoroacetic acid. A Perkin-Elmer preparative column was used for HPLC; a 3.5 cm × 28 cm column was packed with octadecylsilane, and the reconstituted material was introduced. A flow rate of 6.0 ml/min was set. The machine was programmed to deliver a ethanol-in-water linear input gradient, starting at 0% ethanol and reaching 50% at 30 minutes.

Absorbance was monitored at 254 mm, 0.1 Absorbance Units=Full Scale. Three major peaks were observed, which respectively eluted at 10.4–10.6 min, 14.0–16.0 min, and 18.0–19.0 min. The biological activity was assayed and found to reside almost entirely in the material associated with the middle peak, which is designated herein as Beta-1.1. The last peak was found to be associated with material that was mainly phenylalanine and contained approximately 90% of the starting material used. The first peak was lower than the second and third, in terms of absorbance units, and is believed to be an artifact of the system associated with the ethanol solvent or due to elution of salts. The second and third peaks varied in relative height from preparation to preparation.

Based on refractive index measurements, the ethanol concentration of the effluent of the second peak was found to be from approximately 0.1% to approximately 0.4%.

An amino acid assay of the material associated with the Beta-1.1 peak was made, with the following normalized results:

| | |
|---|---|
| Asx | 2 |
| Thr | 1 |
| Ser | 1 |
| Glx | 1 |
| Pro | 2 |
| Gly | 4 |
| Ala | 2 |
| Val | 1 |
| Ile | 1 |
| Tyr | 1 |
| Lys | 3 |
| His | 1 |
| Arg | 1 |
| | 23 |

For a number of reasons, the inventor did not believe that the Beta-1.1 endogenous amplifier material was a polypeptide with 23 peptide groups, or a mixture of 3 octapeptides, or the like. The inventor determined that still further purification of the materials of the foregoing process would be desirable, to ascertain whether one or more immunologically active materials were present in which there were substantially fewer peptide groups.

To date, this has resulted in the extraction of two peptide materials having about ten times greater intrinsic amplifier activity than Beta-1.0 or Beta-1.1 per unit weight of material: a dipeptide material and a tripeptide material. A third material was extracted, which appears to be a nonpeptide. An acetonitrile HPLC process was developed that permitted such a result and it is described in the following example. Best results were obtained with a Dupont brand of resin column (known as ZORBAX TM ), which comes packed with a Dupont material containing octadecylsilane groups chemically bonded to silica particles. All references to HPLC resin columns hereafter should be understood to refer to the foregoing type of Dupont material.

EXAMPLE 5

Purification of Beta-1.1 to Beta-1.11, Beta-1.12, and Beta-1.13

The Beta-1.1 material of Example 4 was injected into an HPLC resin column, 1 ml/min flow rate, 25° C. The solvent system was 100% acetonitrile ($CH_3CN$), HPLC Grade, and 0.05% trifluoroacetic acid aqueous solution, HPLC Grade, pH 2.5. The following solvent input linear gradients were used: (1) for 15 minutes, from 0–6% acetonitrile; (2) for 30 minutes, from 6–40% acetonitrile.

A fraction of interest, hereinafter designated as Beta-1.11, eluted at approximately 23.8 to 24.8 min, for a new column. It was associated with a sharp, narrow peak of UV absorption at 210 nm; this peak is approximately the fourth absorption peak observed (some variability existing). The material was lyophilized and reconstituted in normal saline, and set aside for further use. As shown below, Beta-1.11 contains endogenous YG-material.

Another fraction of interest, eluted from this material on this column, but somewhat irregularly. When it eluted, the retention time was approximately 22.8–23.2 min. It was associated with a distinct peak of ultraviolet absorption at 210 nm, a third peak which is just before the peak associ-ated with Beta-1.11, and which often partially overlaps with the third peak. The material was lyophilized and reconstituted in normal saline, and set aside for further use. As shown below, this material, hereinafter referred to as Beta-1.12, contains endogenous YGG-material.

A fifth UV peak is associated with material having no demonstrated intrinsic activity. A sixth UV peak is associated with phenylalanine. A seventh peak, discussed below, is associated with immunologically active material of as-yet undefined structure.

Other moieties found present in effluents of this process were Gly-Gly, Ser-Phe, and Ala, along with possibly other amino acid residues as well. None of these other moieties appeared to possess immunological activity, as assayed by DH test.

To avoid confusion between the first two moieties of interest, particularly in the case of aged columns, it has been found advantageous to run purified commercial YGG through the column as a marker. Such YGG elutes reproducibly 0.8 to 1.2 min before Beta-1.11 (approximately the same zone as Beta-1.12).

Finally, another fraction of interest is eluted from the material on this column, at a retention time of approximately 31.5 min. It was associated with a sharp peak of UV absorption at 210 nm, a seventh peak considerably after the third and fourth peaks associated with Beta-1.11 and Beta-1.12. As discussed below, this material, hereinafter referred to as Beta-1.13, is immunologically active.

The endogenous amplifiers of this invention

The Beta-1.11 material was then subjected to amino acid sequencing procedures. Using standard techniques, such as those described in Example 4 of Gottlieb U.S. Pat. No. 4,699,898, it was determined that Beta-1.11 contains Tyr and Gly, which come off in that order, in approximately equal proportions. This indicated the presence of a YG-material. (A protein/peptide sequencer automatically removes one amino acid at a time from the N-terminal end of a protein or peptide for determination of amino acid sequence.) It was thus ascertained that Beta-1.11 is endogenous YG-material. (Those two terms are interchangeable for the purposes of this specification.)

Some YGG-material was also detected in this material, which has been found to be immunologically active, as is discussed below. Small amounts of Ile and Lys were also detected. Those may be artifacts of the procedure, or may indicate small amounts of Ile/Lys components in a molecule or molecules present in relatively low concentrations in the product (such as, hypothetically, Tyr-Ile-Lys, Tyr-Gly-Lys, Tyr-Gly-Gly-Ile). The inventor presently believes that the Ile/Lys material is simply an artifact or a nonsignificant component.

The Beta-1.12 material was also subjected to amino acid sequencing procedures and was identified as containing a Tyr-Gly-Gly amino acid residue sequence, indicating the presence of a YGG-material. It was thus ascertained that Beta-1.12 is endogenous YGG-material. (Those two terms are interchangeable for the purposes of this specification.)

It has not been ascertained whether isomeric forms are present, whether the YG- and YGG-materials of Beta-1.11 and 1.12 have other groups bound to them (e.g., methyl, acetyl, amide), or whether complexes with metal ions (such as, possibly, $Zn++$, $Ca++$, $Fe++$, $Mn++$, or $Mg++$) are present, and if so whether the different forms, if any, possess different immunological activity. While it would be desirable to ascertain this, the present state of the art makes it difficult or impossible to do so.

As indicated below, certain immunological assay data indicates that Beta-1.11 and Beta-1.12 are in some way different from chemically manufactured (synthetic) YG and YGG, respectively, because the endogenous products extracted from human leukocyte material appear to have greater immunological activity than the purified synthetic peptide chemicals. (The purified chemicals are not dimerized and they are not complexed with $Zn++$ or other metallic ions. But the endogenous products may have such structural variations.)

There is reason to infer that the naturally occurring Beta-1.11 and 1.12 amplifier products are present in the human or animal body in the form of a complex of $(X)M++(Y)$, where $(X)$ and $(Y)$ are each selected from the group consisting of Tyr-Gly, Tyr-Gly-Gly, or a derivative thereof, and where $M++$ is $Zn++$ or another divalent metallic ion such as $Ca++$, $Fe++$, $Mn++$, or $Mg++$. There is a negative site on the Tyr group that may bind to the $M++$ ion; there is also a C-terminal negative site on the last Gly that may so bind. There may well also be a mixture of such complexes.

Work was done to ascertain the ratio of Tyr-Gly and Tyr-Gly-Gly components in human materials, by radioiodinating the Tyr groups and then separating the Tyr-Gly and Tyr-Gly-Gly moieties by gel electrophoresis to permit the respective amounts to be compared. If there were only a $(Tyr-Gly)M++(Tyr-Gly-Gly)$ complex, one could anticipate a constant 1:1 ratio of YG and YGG. But that does not occur; instead, the proportions observed varied from sample to sample, but averaged YG:YGG = 18:1. Possibly, there are several different materials or complexes—such as $(Tyr-Gly)M++(Tyr-Gly)$, $(Tyr-Gly)M++(Tyr-Gly-Gly)$, and $(Tyr-Gly-Gly)M++(Tyr-Gly-Gly)$—in varying proportions, depending on as yet unidentified physiological parameters.

From the foregoing amino acid sequencing data, in conjunction with biological assay data described below, the inventor concludes as follows: Two biologically significant components of the Beta-1.1 material described above may be further characterized as containing the amino acids Tyr and Gly, in a 1:1 ratio (YG) or 1:2 ratio (YGG), and as not containing substantial amounts of any other amino acid. The YG- and YGG-materials present in the Beta materials may exist as a mixture of variable proportions; either or both molecules may be complexed with metal ions (such as $Zn++$, $Ca++$, $Fe++$, $Mn++$, or $Mg++$); both may be complexed together, with the possible addition of metal ions. The materials eliminated from the final materials, such as Phe (approximately 90% of Beta-1.0), Phe-Ser, Gly-Gly, and Gly-Gly, do not possess intrinsic immunological activity, but they may endogenously co-act with the YG- and YGG-materials to enhance their stability or immunological activity.

The foregoing series of processes began with a leukocyte dialysate containing an extract from approximately $10^{10}$ leukocytes. This yielded approximately 84 ug of Beta-1.0 or, alternatively, somewhat less Beta-1.1. The Beta-1.1 in turn yielded approximately 168 ng of endogenous YG-material and 3 ng of endogenous YGG-material each. A quantity of 1 to 5 pg of endogenous YG-material, which is approximately one clinical dosage unit, as discussed below, therefore was derived from approximately 1 to $2.5 \times 10^5$ leukocytes. (However, the same starting material also yielded about 10% of that amount of endogenous YGG-material.)

The inventor has also discovered the existence of a third immunologically active component in Beta-1.1, designated herein as Beta-1.13. This component elutes from the system of Example 5, as stated above, at approximately 31.5 min, for a new column. It is characterized by a sharp, narrow peak of UV absorption at 210 nm; this peak is approximately the seventh absorption peak observed in the procedure of Example 5. Beta-1.13 is believed to be a ring product, not a peptide, having a M.W. of approximately 250 to 300. It has not been established, however, that Beta-1.13 is not a peptide. Beta-1.13 has occurred in leukocyte dialysate samples in what appears to be approximately the same amount as did Beta-1.12 (i.e., 5% to 10% as much as Beta-1.11). The inventor believes that Beta-1.13 is a single molecular species, not a mixture of different molecular species, but that fact has not as yet been proved. At this point, the inventor considers that he has disclosed how to make Beta-1.13, and hereinafter the inventor describes how to use Beta-1.13 as an amplifier of the human immune system.

II. Human Biological Assay Data

Additional biological assay methods have been developed, which were not described in Gottlieb U.S. Pat. No. 4,468,379, Gottlieb U.S. Pat. No. 4,616,079 (of which this application is a continuation-in-part), or Gottlieb U.S. Pat. No. 4,699,898. The following additional assay methods have now been found advantageous:

(1) antigen-induced enhanced "leukocyte inhibitory factor" ("LIF");
(2) augmented production of interleukin-2 ("IL-2"), stimulated by mitogen, antigen, or alloantigen;
(3) enhanced generation of cytotoxic cells to Raji cells (a tumor line which grows in culture);
(4) augmented production of gamma-interferon, stimulated by mitogen or antigen; and
(5) enhanced expression of high-density receptors for IL-2.

The inventor has found that Beta-1.0 and Zeta-2 displayed at least three out of the five new assay criteria as well as the enhanced DH response. However, since these materials are endogenous rather than synthetic, they vary in biological activity from time to time and depending on donor population.

The LIF assay is described in Gottlieb et al., *Modulation of Human T Cell Production of Migration Inhibitory Lymphokines*, J. Immunology 132: 256–260 (Jan. 1984), at p. 257. Protocols for the other assays are believed to be known to those skilled in this art.

As stated above, it has been shown that materials of the preceding examples have amplifier activity. The following examples illustrate this.

EXAMPLE 6

DH Assay of Beta-1.0

Serial dilutions of Beta-1.0 of preceding Example 2 were made from a solution containing the amplifier material derived from approximately $4 \times 10^8$ buffy coat leukocytes in 1 ml of aqueous saline solution.

Tetanus toxoid was selected as the antigen to challenge the immune system of the patient. To 0.05 ml of tetanus toxoid, fluid diluted to 1/10 to 1/40 so as to elicit a small (preferably slightly less than $5 \times 5$ mm) skin reaction from the patient, 0.1 ml of the diluted Beta-1.0 preparation was added. The patient was subcutaneously injected with several different dilutions of Beta-1.0, and also with an equal quantity of tetanus toxoid (TT) without any Beta-1.0 added thereto. Two approximately perpendicular diameters of each responding skin site on the man's arm were measured at the times indicated below. ("TT+_" refers to TT and a dilution of Beta to the concentration indicated; "TT" alone is TT without Beta-1.0.)

At 5 hours, the respective responses to $TT+10^{-8}$, $TT+10^{-9}$, and TT were $14 \times 14$ mm, $19 \times 14$, and $3 \times 3$. At 24 hours: $20 \times 24$ mm, $19 \times 23$, $14 \times 12$. Other dilutions of Beta-1.0 produced less response.

EXAMPLE 7

DH Assay of Beta-1.11

Example 6 was with serial dilutions of Beta-1.11 (endogenous YG-material), beginning with 1 microgram per microliter (ug/ul) of the product of Example 5. It is estimated that 168 ug of the product of Example 5 is the amount of Beta-1.11 that can be derived from approximately $1 \times 10^{10}$ buffy coat leukocytes. It is also estimated that the M.W. of Beta-1.11 is approximately 239. Hence, 1 ug/ul is approximately a 4 mM. solution. Dilutions to 4 fM and 0.4 fM were prepared.

After following the procedure described in Example 6, it was observed that at 5 hours, the respective responses to TT+0.1 ml 4 fM, TT+0.1 ml 0.4 fM, and TT were $7 \times 8$ mm, $9 \times 9$, and $3 \times 5$. At 24 hours: $18 \times 21$ mm, $19 \times 19$, $14 \times 15$. Other dilutions of Beta-1.11 produced less response.

EXAMPLE 7A

Second Beta-1.11 DH Assay

Example 7 was repeated with serial dilutions of Beta-1.11 (endogenous YG-material), beginning with 53 nM solution of the product of Example 5. Serial dilutions of $10^{-6}$, $10^{-7}$, $10^{-8}$, and $10^{-9}$ were prepared, a saline control was also used. TT was diluted 1/20. Erythema was measured (mm $\times$ mm) and induration was scored on a scale of 0 to $+++$. The following data were observed (and are published in Sinha et al., Biotech 6:810–15 (1988), at p. 812):

| | Hours Post Injection | | | |
| | 7 Hrs | | 12 Hrs | |
| Dilution | Erythema | Indur. | Erythema | Indur. |
| --- | --- | --- | --- | --- |
| $10^{-6}$ | $14 \times 10$ | 0 | $18 \times 18$ | 0 |
| $10^{-7}$ | $12 \times 15$ | + | $15 \times 25$ | 0 |
| $10^{-8}$ | $12 \times 17$ | ++ | $20 \times 22$ | 0 |
| $10^{-9}$ | $10 \times 12$ | + | $20 \times 21$ | ± |
| Saline Ctl. | $4 \times 5$ | 0 | $10 \times 10$ | 0 |

EXAMPLE 8

DH Assay of Beta-1.12

Example 6 was repeated with serial dilutions of Beta-1.12 (endogenous YGG-material), beginning with 1 ug/ul of the product of Example 5. It is estimated that 3 ng of the product of Example 5 is the amount of Beta-1.12 that can be derived from approximately $1 \times 10^{10}$ buffy coat leukocytes. It is also estimated that the M.W. of Beta-1.12 is approximately 295. Hence, 1 ug/ul is approximately a 3 mM solution. Dilutions to 3 fM and 0.3 fM were prepared.

After following the procedure described in Example 6, it was observed that at 5 hours, the respective responses to TT+0.1 ml 3 fM, TT+0.1 ml 0.3 fM, and TT were $7 \times 8$ mm, $9 \times 9$, and $3 \times 5$. At 24 hours: $18 \times 21$ mm, $19 \times 19$, $14 \times 15$. Other dilutions of Beta-1.12 produced less response.

EXAMPLE 8A

Second Beta-1.12 DH Assay

Example 8 was repeated with serial dilutions of Beta-1.12 (endogenous YGG-material), beginning with 64 nM solution of the product of Example 5. Serial dilutions of $10^{-6}$, $10^{-7}$, $10^{-8}$, and $10^{-9}$ were prepared; two saline controls were also used. TT was diluted 1/80. Erythema was measured (mm×mm) and induration was scored on a scale of 0 to +++. The following data were observed (and are published in Sinha et al., Biotech 6:810-15 (1988), at p. 812):

|  | Hours Post Injection | | | |
|---|---|---|---|---|
|  | 7 Hrs | | 12 Hrs | |
| Dilution | Erythema | Indur. | Erythema | Indur. |
| $10^{-6}$ | 2 × 2 | 0 | 0 | 0 |
| $10^{-7}$ | 9 × 10 | + | 16 × 16 | + |
| $10^{-8}$ | 12 × 13 | ++ | 18 × 21 | ++ |
| $10^{-9}$ | 10 × 13 | ++ | 16 × 17 | + |
| L Saline Ctl. | 8 × 10 | + | 16 × 17 | + |
| R Saline Ctl. | 8 × 8 | + | 16 × 17 | + |

EXAMPLE 8B

DH Assay of Beta-1.13

Example 6 was repeated with serial dilutions of Beta-1.13 (third endogenous material), beginning with 1 ug/ul of the product of Example 5. It is estimated that 3 ng of the product of Example 5 is the amount of Beta-1.13 that can be derived from approximately $1 \times 10^{10}$ buffy coat leukocytes. It is also estimated that the M.W. of Beta-1.13 is approximately 400. Hence, 1 ug/ul is approximately a 2.5 mM solution. Dilutions to 2.5 fM and 0.25 fM were prepared.

After following the procedure described in Example 6, it was observed that at 7 hours, the re-spective responses to TT+0.1 ml 2.5 fM, TT+0.1 ml 0.25 fM, and TT were 11×17 mm, 10×16, and 9 ×9. At 24 hours: 13×12 mm, 14×12, 6×9. Other dilutions of Beta-1.13 produced less response.

EXAMPLE 9

Effect of Beta-1.11 on T-helper Cell IL-2 Receptor Expression

Serial dilutions of Beta-1.11 were prepared, beginning with a 81.3 nM concentration and then serially diluting that further by factors of 1000, 2000, 4000 . . . 512,000. The 1/512,000 dilution produces a preparation that is a 159 fM concentration of Beta-1.11.

A tetanus toxoid (TT) preparation was prepared of strength 0.1 flocculation unit ($L_f$) per ml.

Cell cultures were prepared with the TT preparation alone, and with the TT preparation combined with the serial dilutions of Beta-1.11. The cultures were incubated and mixed with a suitable antibody against IL-2 receptors. Data for receptor expression was tabulated both for T-helper cells bearing a low density of receptors and for T-helper cells bearing a high density of receptors. (The T-helper cells bearing a high density of receptors are considered to be the ones that are immunologically active.) The cells were from normal subjects.

In the case of the TT preparation alone, 4.7% of T-helper cells expressed a low density of IL-2 receptors and 0.40% of T-helper cells expressed a high density of IL-2 receptors.

There was a plateau of maximal expression for T-helper cells bearing a low density of receptors from TT+20.3 pM Beta-1.11 (9.9% expression) to TT +1.3 pM (8.4%). The highest figure for high density of receptors was at 159 fM (9.9%). This highest figure occurred at a point where there was a steadily ascending curve. Accordingly, it is believed that if further dilutions of Beta-1.11 had been used a still higher figure would have been reached, before the expression percentage began to drop. It is not possible to state, from this data, where the maximum would occur, but it seems likely to be somewhere between 80 fM and 20 fM.

The low density plateau reflected an approximately doubled expression rate of IL-2 receptors as a result of Beta-1.11. The high density maximum, which the inventor considers more relevant, reflected an increase of IL-2 receptors by a factor of approximately 25 as a result of Beta-1.11, and that figure probably falls short of the increase that would result from using still more diluted Beta-1.11.

EXAMPLE 10

Effect of Beta-1.11 on Antigen-Induced Production of Gamma Interferon

Preparations of 0.1 $L_f$/ml and 1.0 Lf/ml TT were used to determine the effect of Beta-1.11 (endogenous YG-material) on production of gamma-interferon in normal cells. As before, serial dilutions of Beta-1.11 were prepared from 46.5 pM to 91 fM.

The 0.1 $L_f$/ml and 1.0 Lf/ml TT preparations, alone, respectively induced baseline production of 1.0 and 10.4 units/ml of gamma-interferon.

0.1 $L_f$/ml TT+317 fM Beta-1.11 produced 29.8 units/ml, the observed maximum, and 0.1 $L_f$/ml TT+159 fM Beta-1.11 produced 29.1 units/ml.

1.0 $L_f$/ml TT+159 fM produced 25.6 units/ml, the maximum.

In the case of the 0.1 $L_f$/ml TT preparation, the maximum was approximately 30 times the baseline amount. In the case of the 1.0 $L_f$/ml TT preparation, the maximum was approximately 2.5 times the baseline amount.

Generally, the DH assays showed that Beta-1.11, Beta-1.12, and Beta-1.13 are immunologically active and they appear to be more active (per unit weight) than Beta-1.0. The apparent increase in potency may be attributed to the elimination of phenylalanine and other amino acid products, which are without intrinsic immunological activity.

In both of the TT+Beta-1.11 in vitro immunological tests, expression of high-density IL-2 receptors and antigen-induced production of gamma-interferon, the optimal concentration of Beta-1.11 appeared to be approximately 317 fM for gamma-interferon, and approximately 159 fM for high-density IL-2 receptors. Since these two assays are considered generally indicative of immunological effect, and are found correlated to clinical immunological effect in the case of other Beta materials from which Beta-1.11 is derived, it is considered that the assays indicate a high probability that Beta-1.11 can produce in vivo amplifier effect in human subjects. As shown below, this has been confirmed by clinical data (see Examples 17-18). Thus, the materials of this invention have been shown to stimulate gamma-interferon production and to enhance production of receptors of IL-2. These are among the most important known effects of modifiers of biological responses produced in lymphocytes.

In the case of Beta-1.12, it is not certain whether the DH response is to the Beta-1.12 per se (i.e., to material essentially consisting of endogenous YGG-material) or to a Beta-1.11 metabolite (i.e., material consisting essentially of endogenous YG-material) of Beta-1.12. It is known that pentapeptides (enkephalins) containing a YGG amino acid residue sequence are degraded in vivo by the action of dipeptidylaminopeptidase, which hydrolyzes enkephalins (e.g., H$_2$N-Tyr-Gly-Gly-Phe-Met-OH) by cleaving the Gly-Gly amide bond. (See, e.g., Schwartz et al., op. cit. supra (Background section of specification), at p. 1716, citing and summarizing studies in this field.) Hence the apparent immunoamplificatory effect of YGG-material might be attributable to YG-material as a metabolite of YGG-material rather than to YGG-material itself.

On the other hand, both of these endogenous peptide materials may have intrinsic immunoamplificatory effect. For example, the receptor site for this lymphokine could be associated with the Tyr-Gly portion of the molecule, and the additional Gly amino acid residue may have a neutral effect on reception and biological activity. It is also possible that YGG interacts with a different receptor site to have the same biological effect as YG. Alternatively, a complex of both peptides, perhaps through a trace metal (such as $Zn++$, $Ca++$, $Fe++$, $Mn++$, or $Mg++$) may be required. This is a question calling for further work, such as in vitro tests of Tyr-Gly-Gly in the presence of a suitable aminopeptidase inhibitor, to prevent cleavage of the Gly-Gly amide bond in Tyr-Gly-Gly to produce Tyr-Gly.

In the case of Beta-1.13, the entire immunological activity is attributed to Beta-1.13 itself, since there is no reason to consider its molecule to be a metabolite of either of the peptide molecules, which appear to be smaller molecules than Beta-1.13.

The availability of the in vitro assays described above (see Examples 9–10) has suggested that a comparison might be made of the relative immunological activity of various samples of amplifier 1 (see Example 3). Since it is known that the constituent amplifiers within amplifier 1 occur in varying proportions, depending on the particular sample, and the inventor has observed that different preparations of amplifier 1 appear to vary in immunological activity as measured by such means as DH tests, it would appear to be of interest to ascertain whether variation in immunological activity is capable of measurement by in vivo assay. It is noted, however, that in vivo or clinical tests on patients for this purpose are not feasible, for legal and moral reasons. It is not feasible to ascertain repeatability of clinical results by testing a product in human beings simply to satisfy one's curiosity, and no practical animal model has been demonstrated to exist for assays of this type. However, it is generally recognized among immunologists that certain in vitro assays, using human-derived materials, are considered to be important predictors of clinical results. The assays described in Examples 9–10 are, in the inventor's opinion, important such predictors.

EXAMPLE 11

Comparison Assays, Amplifier 1

Portions of the five different samples of amplifier 1, of Example 3, are subjected to the T-helper cell receptor expression test of Example 9. It is found that the results vary from sample to sample, so that in comparison with the mean, the maximum to minimum range of immunological activity is approximately plus or minus 75%.

Portions of the five different samples of amplifier 1, of Example 3, are subjected to the antigen-induced production of gamma interferon assay of Example 10. It is found that the results vary from sample to sample, so that in comparison with the mean, the maximum to minimum range of immunological activity is approximately plus or minus 70%.

As a control, the same sample of amplifier 1 is successively subjected to the same assay five times. It is found that the results vary from test to test, so that in comparison with the mean, the maximum to minimum range of immunological activity is approximately plus or minus 25%.

The variation in activity among the five different samples is attributed to the variation in amplifier content of the samples.

III. Human Therapy Tests of Endogenous Amplifier Materials

The effectiveness of above-described endogenous amplifier materials in amplifying human immune system response has been tested in a number of men suffering from AIDS or ARC. All amplifier materials used in this work were free of endotoxin as detected by the Limulus assay (M.A. Bioproducts, Rockville, Md.). All material used was also pyrogen-free. The following examples illustrate these tests. (As used hereinafter, the term "T-helper cell" includes cells designated as $T4^+$, $CD4^+$, $Leu3^+$, and T4.)

The inventor has ascertained by empirical means that an effective dosage amount of these products, in the procedures described hereinafter, is that derived from 125,000 leukocytes, purified by the method of Example 2 and dispensed in 0.5 ml of normal sterile saline solution. (This dosage amount, that derived from $1.25 \times 10^5$ leukocytes, is frequently referred to hereinafter as "one standard dose of Beta." When that term is used in the following examples, it means the amount of Beta-1.0 derived from 125,000 leukocytes by the method of Example 2.)

EXAMPLE 12

Multiple Doses of Beta-1.0 With Transfusion

An AIDS patient, DT, with Kaposi's sarcoma was given doses of Beta-1.0 (a preparation containing YG-material, YGG-material, phenylalanine, and other materials) together with transfusions of isologous leukocytes available from DT's identical twin brother (a normal, disease-free person). DT also received such transfusions without Beta-1.0.

An initial transfusion of approximately $1.0 \times 10^{10}$ isologous leukocytes (without Beta-1.0) produced a moderate restoration of DT's phytohemagglutin (PHA) proliferative response. Within 13 days the response declined to baseline levels with no concomitant alteration in the ratio of circulating helper leukocytes to suppressor leukocytes (T4/T8 ratio).

Ten days after the initial transfusion, DT was given a single standard dose of Beta-1.0. No effect was observed on DT's PHA response.

A cycle of treatment comprised of a second isologous leukocyte transfusion (again, the same number of leukocytes) followed at 24, 48, and 71 hours by subcutaneous administration of Beta-1.0 doses derived from 400,000, 4,000,000, and 400,000 leukocytes, respectively (i.e., 3.2, 32, and 3.2 standard doses). A significant increase in DT's PHA responsiveness followed. It was associated with an increase in the T4/T8 ratio, resulting from an absolute increase of T4+ cells and a decrease in T8+ cell numbers. After approximately one month, these parameters of immune system response declined to approximately their former level.

A third transfusion similar to the first (no Beta-1.0) was given. No effect on PHA response or T4/T8 ratio was observed.

While these studies were made, parallel studies of IL-2 production were made. Initially, no IL-2 production was observed in response to PHA. This correlated with the patient's low proliferative response to mitogen. The initial leukocyte transfusion did not affect this parameter. After the second transfusion (leukocytes and Beta-1.0), significant levels of IL-2 were induced by PHA. It is considered that this data (and similar data in the next two examples) confirms the in vitro data of Examples 9–10 and the discussion following those examples, concerning stimulation of lymphokine production.

EXAMPLE 13

Multiple Doses of Beta-1.0: Group 1

The members of a group of 15 patients with AIDS or ARC received one standard dose of Beta-1.0 once every month until three doses were given (three months). Of these 15 patients, six had candida infections (oral candidiasis), and 12 had Kaposi's Sarcoma.

Clinical symptoms were monitored. No decrease in weight was observed. No toxicity to Beta-1.0 was observed.

A significant decrease in candida infection was observed as a result of treatment, in three-quarters of the patients completing the monthly dose protocol.

Skin test sensitivity (DH test) to tetanus toxoid was noticeably enhanced, and may be considered to have returned to an approximately normal level in 47% of the subjects. Since, according to the Walter Reed Classification of Severity of AIDS/ARC (see 314 New Eng. J. Med. 131 (1986)), candida infection and loss of skin test sensitivity are signs of far advanced immunodeficiency, it is considered that the effectiveness of Beta-1.0 in reversing these symptoms is medically significant.

Mitogen-stimulated leukocyte proliferation increased with each successive dose. Mitogen-stimulated IL-2 production increased in at least 60% of patients. Response to pokeweed mitogen (PWM) increased for those patients having more than 50–100 T4 cells per $mm^3$ remaining.

EXAMPLE 14

Multiple Doses of Beta-1.0: Group 2

The members of a group of 14 patients with AIDS or ARC received one standard dose of Beta-1.0 every two weeks for six doses (approximately three months). Of these subjects, six had candida infections. Of the 14 patients, 11 had Kaposi's Sarcoma.

Clinical symptoms were monitored. Eleven of the 14 patients gained weight. An average weight gain of 4.4 lb occurred in these 11. No toxicity to Beta-1.0 was observed. Serum uric acid levels fell. Creatine phosphokinase levels fell. Since high levels of uric acid and creatine phosphokinase reflect tissue breakdown characteristic of AIDS, it is considered that lowering of the levels of these substances and reversal of weight loss suggests significant clinical improvement.

Skin test sensitivity to tetanus toxoid returned in 57% of subjects. Candida infection was totally cleared in three subjects and decreased in another.

Mitogen-stimulated leukocyte proliferation increased. Mitogen-stimulated IL-2 production increased in 60% of patients after two doses of Beta-1.0; and in all those patients having more than 50–100 T-helper cells/$mm^3$ remaining, after two doses of Beta-1.0.

Response to pokeweed mitogen (PWM) increased for those patients having more than 50–100 T-helper cells/$mm^3$ remaining. A small increase to PWM appeared after the second dose with those patients having fewer than 50–100 T-helper cells/$mm^3$ remaining, and slowly increased following the next two doses.

We also observed a slowing of the rate of destruction of T-helper cells in these AIDS and ARC patients during their treatment with Beta-1.0. For example, untreated patients with ARC typically lose T-helper cells at the rate of approximately 13.4 cells/month. For those ARC patients who received Beta-1.0 on a monthly basis (Example 13), the rate of T-helper cell loss was 7.2 cells/month, while for those who received it every two weeks (Example 14) the rate of T-helper cell loss was 4.2 cells/month. It is believed that this data indicates that Beta-1.0 slows the rate of T-helper cell destruction typical of ARC, and that the retarding of destruction was proportional here to the dosage.

EXAMPLE 15

Multiple Doses of Beta-1.0: Group 3

Five patients, three with AIDS (RB, JB, and RG) and two with ARC (WW and CM) were treated with Beta-1.0 over a period of approximately a year or more. (One standard dose administered intradermally every two weeks.)

Skin test sensitivity returned completely in three subjects and partially in one (RB, JB, WW, and CM). Candida infection improved in the two patients (RB and CM) initially having it and it did not appear in the others. The percentage of T-helper cells increased transiently in four patients (RB, RG, WW, and CM).

Three patients gained substantial weight (RB, WW, and CM). PHA-stimulated lymphocyte proliferation increased in all five, PWM response in four (RB, RG, WW and CM), IL-2 production in three (RB, WW, and CM).

A sixth patient was originally included in this group, but his immunodeficiency was so severe on presentation that he succumbed to an overwhelming opportunistic infection before immunological reconstitution could be effected.

EXAMPLE 16

AIDS/ARC Conversion in Placebo-Controlled Multicenter Tests of Beta-1.0

In order to secure clinical data for FDA licensing of Beta-1.0, double-blind, randomized, placebo-controlled trials were conducted on a total of 141 ARC patients at eight testing centers, over a six-month period.

93 patients diagnosed as having ARC received one standard dose of Beta-1.0 biweekly for 26 weeks. 48 patients diagnosed as having ARC received a placebo dose biweekly for 26 weeks. Attending physicians monitored the patients for clinical symptoms.

In particular, focus was directed to diagnosis of the conversion to AIDS in these ARC patients. This conversion is marked by a significant change in symptoms and clinical status, such as development of Pneumocytis carinii pneumonia, tracheobronchial candidiasis, or Kaposi's Sarcoma. Such a clinical event is termed an "endpoint," since it marks the end of ARC and the beginning of AIDS, which appears to be invariably fatal, and is attended by more severe clinical sympotoms.

At the end of 26 weeks, endpoints had appeared in 12 of the 48 placebo patients, representing 25% of that population., and in 4 of the 93 patients given Beta-1.0, representing 4% of that population. The rate of ARC/AIDS conversion in patients treated with Beta-1.0 was thus approximately 20% of the conversion rate in placebo patients. Since ARC/AIDS conversion is clinically highly significant, it is believed that the foregoing trial data supports FDA licensure of Beta-1.0 for ARC patients, to delay conversion to AIDS; and the data has been submitted to FDA for that purpose.

The patients treated with Beta-1.0 in these trials were also observed to show improved clinical symptomatology comparable to that described above in Examples 13–14, such as lessened weight loss, lessened fever, less coughing, and less diarrhea.

EXAMPLE 17

Three-month Dosage of Beta-1.11 (ARC Patient)

ARC patient A received a total of six doses of 0.1 pg of Beta-1.11 (endogenous YG-material), given biweekly for approximately three months. His immune responsiveness was measured by determining the reactivity of his leukocytes to pokeweed mitogen (PWM).

A baseline responsiveness was established before treatment at 6241 units, hereinafter designated as 100%, for comparison purposes. His subsequent PWM reactivity measurements are tabulated below:

| Response after Dose No. | Units | Percent |
|---|---|---|
| 0 (baseline) | 6241 | 100% |
| 1 | 14,027 | 225 |
| 2 | 13,875 | 222 |
| 3 | 12,058 | 193 |
| 4 | 11,753 | 188 |
| 5 | 10,358 | 166 |

It was also observed that A regained his DH reaction to tetanus toxoid as a result of treatment with Beta-1.11. The foregoing data indicated that dosage with endogenous YG-material at least partially reversed this patient's immunodeficiency.

The trend of observed PWM reactivity suggests that the effect of 0.1 pg was less after several doses had been administered, and that lower doses should be used for subsequent treatment. That is, a dose that is optimal on starting therapy will sometimes have to be reduced as time goes on. The inventor has observed that there is an optimal dosage of amplifier, and that doses above or below the optimum amount produce less amplifier effect than the optimal dose does (see, e.g., Gottlieb U.S. Pat. No. 4,468,379, col. 13–14, 16–17; Gottlieb U.S. Pat. No. 4,778,750, Sections III–IV, cols. 5–7). The inventor therefore attributes the results described above to a dosage in higher than optimal amount for this particular person's body, at the time of the treatment described.

EXAMPLE 18

Two-month Dosage of Beta-1.11 (ARC Patient)

ARC patient B had previously been treated with a series of standard doses of Beta-1.0 (a preparation containing endogenous YG-material, endogenous YGG-material, phenylalanine, and other material) to reconstitute his immune system. He was then given biweekly doses of 0.1 pg of Beta-1.11 (endogenous YG-material) for a total of four doses.

His immune function was measured by determining PWM reactivity, as in the case of Patient A. His reactivity throughout remained at slightly below normal levels. His DH response to tetanus toxoid also remained at slightly below normal levels. The foregoing data indicate that dosage with endogenous YG-material maintained in effect the restoration of immune response that had been brought about by his prior dosage with Beta-1.0.

The data for Patient B suggest that 0.1 pg was approximately the correct dosage amount for this patient (i.e., an effective dosage amount).

The foregoing examples suggest that endogenous YG-material (Beta-1.11) and materials containing it (such as Beta-1.0) stimulate the T-helper cell population of the human body. This suggests that Beta materials are useful in improving human immune response characterized by a T-helper cell defect. It is believed that doses of Beta partially restore the functioning of a defective subset of the T-helper lymphocytes. Tests such as that conducted on patient DT suggest that Beta can partially correct a defect in T-helper cell function even in the presence of the excessive proportions of T8+cells observed in AIDS patients. It appears, further, that some minimal level of residual T-helper cell function must be present for Beta to improve immunological functions; if T-helper cell loss is too severe, there may not be enough T-helper cells left to respond to doses of Beta as a lymphokine and thus be immunologically reconstituted. The data above suggest that when the total T-helper cell population falls below approximately 100 cells/mm$^3$, it is difficult or impossible to reconstitute immunological function.

Generally speaking, 0.5 to 5.0 pg of Beta-1.11 (endogenous YG-material) 0.5 to 5 ng of Beta-1.0 (as defined by phenylalanine content), administered biweekly by intradermal or subcutaneous injection, are effective dosage amounts for adult male (70 kg) AIDS or ARC patients. Those dosages are approximately equivalent to 7 kg to YG/kg and 7 to 75 pg/kg of Beta-1.0 (based on phenylalanine content), respectively. Because of patient-to-patient individual variations, the difference in various immunodeficient clinical conditions, and the need to allow exercise of professional judgment by the attending physician, these dosage amounts must be considered subject to change by a factor of 5 to 10 in each direction.

The above-described clinical work has primarily been that conducted with IMREG-1 (Beta-1.0), which has been found to be a mixture of Beta-1.11 (endogenous YG-material), Beta-1.12 (endogenous YGG-material), Beta-1.13, phenylalanine, Phe-Ser, Gly-Gly, Gly-Glu, and amounts of some other amino acid products. It is believed desirable to administer a standardized product to patients, rather than a variable biological product whose constituents differ from dose to dose depending on the source material. Thus, it is considered that it would probably be preferable to administer a predetermined mixture of Beta-1.11 (endogenous YG-material), Beta-1.12 (endogenous YGG-material), and perhaps other material, rather than unstandardized Beta-1.0, subject of course to regulatory constraints.

This suggests a preferred procedure for using endogenous materials in which purification to the Beta-1.11 and Beta-1.12 level would occur, followed by remixture in accordance with a predetermined formula. As indicated elsewhere, the average ratio of YG-material to YGG-material in Beta-1.0 has been found to be approximately 18:1. If, as may be the case, the two amplifiers must be concurrently present for optimal biological results, the predetermined mixture would desirably contain them in approximately that ratio. The inventor considers that this should be subject to a range of from approximately 10:1 to 25:1, parallelling natural variations in the proportion of materials in different human samples.

The foregoing proposed procedure was developed before the inventor's discovery of Beta-1.13 as a third constituent of Beta-1.0. Since then, the inventor discovered that Beta-1.13 was present in approximately the same proportion as Beta-1.12. Hence, the inventor now considers that an approximately 18:1:1 mixture of Beta-1.11, Beta-1.12, and Beta-1.13 would be preferable (i.e., 90%, 5%, and 5% of Beta-1.11, 1.12, and 1.13, respectively).

It is as yet not ascertained whether the phenylalanine, Phe-Ser, Gly-Gly, Gly-Glu, and amounts of some other amino acid products present in Beta-1.0 contribute anything to immunological activity. It has been shown that these components lack detectable intrinsic immunological activity. However, that does not rule out the possibility that they may act as stabilizers, preventers of hydrolysis, or otherwise as adjuncts of the intrinsically active components. Therefore, clinical work may show that the predetermined mixture discussed in the preceding several paragraphs should contain some of these components, which were actually present in the product (Beta-1.0) primarily used in clinical tests with AIDS and ARC patients. Hence, the predetermined mixture may appropriately include phenylalanine, Phe-Ser, Gly-Gly, and Gly-Glu. This would provide a standardized product and yet one more closely parallelling the composition of the natural IMREG-1 material used in large scale clinical tests with AIDS and ARC patients.

It is contemplated that the above described mixture would be packaged in a vial, in a sterile saline solution, or in a prefilled syringe, again in sterile saline. All of the inventor's large-scale clinical work to date has utilized vials of IMREG-1 in sterile saline solution. However, it would be inappropriate to rule out suppositories, or tablets, capsules, and other oral dosage formats, given a suitable delivery mechanism.

The following present-tense example is intended to illustrate and summarize the teachings of the preceding examples, in particular the examples describing actual clinical data with AIDS and ARC patients.

EXAMPLE 19

Increase of Immune Response

A patient is known to suffer from immunodeficiency. The immunodeficiency may be attributed to AIDS, ARC, chemotherapy, radiation treatment, or another known cause of immunodeficiency.

Endogenous amplifiers (Beta-1.11, Beta-1.12, Beta-1.13) are prepared and purified as described in Section I, supra, and are pooled, lyophilized, and redissolved in normal saline or other physiologically acceptable vehicles. An effective dose (e.g., 0.1 ml containing the amount of material extracted from 125,000 leukocytes) is injected intradermally. Increased immune responsiveness occurs and is monitored by the patient's reactivity to an antigen to which he is known to be sensitive (e.g., tetanus toxoid), comparing reactivity before and after administering the amplifiers.

Amplifiers (Beta-1.11, Beta-1.12, Beta-1.13) are further administered either individually, or in combination, depending upon the desired effects. The persistence of the systemic modulation produced by administration of the amplifiers varies from patient to patient, and must therefore be monitored periodically with a suitable sensitivity test, e.g., by DH assay as described above.

Additional doses are administered as required to maintain a desired amplification of immunity, based upon the professional judgment of the attending physician. That is, the dosage should be increased over that specified above, if immune responsiveness is insufficient (but not to the level where increasing doses decrease immune response); and the dosage should be decreased from that specified above, if immune responsiveness is greater than that which the physician considers appropriate.

Zeta-2 was prepared in accordance with Example 1, supra, and Example 5 of U.S. Pat. No. 4,616,079. Mass spectrometer analyses of Zeta-2 did not indicate any peptide components. Although not conclusive, they suggested that Zeta-2 consists essentially of one or more molecules of the prostaglandin family, with blocked hydroxyl groups. It is believed that Zeta-2 has a M.W. of approximately 250 to 300.

Zeta-2 was subjected to DH assay, as described in Example 9 of U.S. Pat. No. 4,616,079. Zeta-2 caused both an accelerated and augmented response to antigen in the DH assay, using PPD on an adult male. Zeta-2 was generally similar to Beta-1.0 in effect but the speed of onset of immunoamplifier activity due to Zeta-2 appeared to be less. In addition to increasing DH response, Zeta-2 was found to increase gamma interferon production and to enhance expression of IL-2 receptors, in vitro. From the foregoing in vivo and in vitro data, which those persons familiar with this field generally regard as important predictors of clinical immune response, the inventor concluded that Zeta-2 possesses immunoamplifier activity similar to that of the Beta group.

EXAMPLE 19A

Zeta-2 Immune Response

The procedure of Example 19 is repeated with another patient known to suffer from immunodeficiency. An effective dose (0.1 ml sterile saline containing the amount of material extracted from 125,000 leukocytes, tested for freedom from endotoxin and pyrogen) is injected intradermally, biweekly for 12 weeks.

The patient's reactivity to PPD (DH assay) increases. Mitogen-stimulated lymphocyte proliferation progressively increases with additional dosages. Mitogen-stimulated IL-2 production also increases.

The patient is retested six weeks after conclusion of the 12-week course. Reactivity to PPD, mitogen-stimulated lymphocyte proliferation, and mitogen-stimulated IL-2 production are found to be at approximately the initial (week-0) level.

It is concluded that administration of Zeta-2 increases immune responsiveness in the patient.

IV. Other Tests and Assays

Other tests and assays are described below that relate to the preparation and testing of these materials so that they are acceptable for therapeutic use, consistent with U.S. legal and regulatory requirements.

EXAMPLE 20

Purification Tests

A sample of Beta-1.0 prepared in accordance with Example 2 is subjected to the Limulus assay for endotoxin (M.A. Bioproducts, Rockville, Md.). The sample is found to be free of endotoxin. The same sample is tested for pyrogen and is found to be free of pyrogen.

A sample of Beta-1.1 prepared in accordance with Example 4 is subjected to the Limulus assay for endotoxin (M.A. Bioproducts, Rockville, Md.). The sample is found to be free of endotoxin. The same sample is tested for pyrogen and is found to be free of pyrogen.

A sample of Beta-1.11 prepared in accordance with Example 5 is subjected to the Limulus assay for endotoxin (M.A. Bioproducts, Rockville, Md.). The sample is found to be free of endotoxin. The same sample is tested for pyrogen and is found to be free of pyrogen.

A sample of Beta-1.12 prepared in accordance with Example 5 is subjected to the Limulus assay for endotoxin (M.A. Bioproducts, Rockville, Md.). The sample is found to be free of endotoxin. The same sample is tested for pyrogen and is found to be free of pyrogen.

A sample of Beta-1.13 prepared in accordance with Example 5 is subjected to the Limulus assay for endotoxin (M.A. Bioproducts, Rockville, Md.). The sample is found to be free of endotoxin. The same sample is tested for pyrogen and is found to be free of pyrogen.

A sample of commercial L-tyrosylglycine (Tyr-Gly), procured from Sigma Chem. Co., St. Louis, Mo., is subjected to the foregoing assays. It is found to contain endotoxin and pyrogen.

A sample of commercial L-tyrosylglycylglycine (Tyr-Gly-Gly), procured from Sigma Chem. Co., St. Louis, Mo., is subjected to the foregoing assays. It is found to contain endotoxin and pyrogen.

Met-enkephalin (Aldrich Chem. Co., St. Louis, Mo.) and peptidyldipeptide hydrolase (ACE) are mixed to cleave the Gly-Phe amide bond as described in Schwartz et al., *Biological inactivation of enkephalins and the role of enkephalin-dipeptidylcarboxypeptidase ("enkephalinase") as neuropeptidase*, 29 Enkephalin Metabolism 1715, 1723 (1981); see also Erdos et al., 27 Biochem. Pharmacol. 843–48 (2978). The mixture is subjected to the foregoing assays, and is found to contain endotoxin and pyrogen. The procedure is repeated with Leu-enkephalin (Aldrich), and the same results occur.

Leu-enkephalin (Aldrich) and enkephalin-dipeptidylcarboxypeptidase are mixed to cleave the Gly-Phe amide bond as described in Schwartz et al., op. cit. supra; see also Schwartz et al., 22 Adv. Biochem. Psychopharm. 219–235 (1980). The mixture is subjected to the foregoing assays, and is found to contain endotoxin and pyrogen.

An alternative procedure has been developed for standardizing Beta-1.0, Beta-1.1, Beta-1.11, and Beta-1.12. The standardization procedure described earlier was to base a dosage unit on the number of leukocytes used to prepare the dosage amount (125,000). The alternative is to measure the amount of YG or YGG present in a sample by radioiodinating the Tyr residue in the sample and comparing with a standard; and then to standardize the sample as desired, on the basis of a predetermined weight per volume or concentration of YG or YGG, the end concentration being controlled by addition of an appropriate amount of sterile saline to dilute the sample to the desired concentration. (A more detailed description of the exact procedure is set forth in the assignee's copending Ser. No. 321,718, Method for separating and quantitating tyrosine-containing small peptides in physiological samples.)

Thus, at the end of section I of this specification it was indicated that approximately 3 pg of endogenous YG-material and approximately 50 fg of endogenous YGG-material is derived from 125,000 leukocytes. Therefore, an amount of Beta-1.11 containing 3 pg of Tyr-Gly can be defined to be a standard dosage unit. Similarly, an amount of Beta-1.0 or Beta-1.1 containing 3 pg of Tyr-Gly can be defined to be a standard dosage unit or a standardized concentration of such products. As used hereinafter, standardized Beta-1.0, Beta-1.1, and Beta-1.11 refer to a sample of such material that contains 3 pg of Tyr-Gly in 0.1 ml of sterile saline (i.e., a concentration of 30 pg/ml), as measured by a radioiodinated Tyr assay as described above.

EXAMPLE 21

Repeatability Tests

The procedure Example 11 is repeated with five samples of standardized Beta-1.0 prepared over a six month interval from available leukocyte sources. It is found that the results of the antigen-induced production of gamma interferon assay vary from sample to sample, so that in comparison with the mean, the maximum to minimum range of immunological activity is approximately plus or minus 35%. As a control, one of the same samples is successively subjected to the same assay five times. It is found that the results vary from test to test, so that in comparison with the mean, the maximum to minimum range of immunological activity is approximately plus or minus 20%.

The procedure of Example 11 is repeated with five samples of standardized Beta-1.1 prepared over a six month interval from available leukocyte sources. It is found that the results of the antigen-induced production of gamma interferon assay vary from sample to sample, so that in comparison with the mean, the maximum to minimum range of immunological activity is approximately plus or minus 30%. As a control, one of the same samples is successively subjected to the same assay five times. It is found that the results vary from test to test, so that in comparison with the mean, the maximum to minimum range of immunological activity is approximately plus or minus 20%.

The procedure of Example 11 is repeated with five samples of standardized Beta-1.11 prepared over a six month interval from available leukocyte sources. It is found that the results of the antigen-induced production of gamma interferon assay vary from sample to sample, so that in comparison with the mean, the maximum to minimum range of immunological activity is approximately plus or minus 25%. As a control, one of the same samples is successively subjected to the same assay five times. It is found that the results vary from test to test, so that in comparison with the mean, the maximum to minimum range of immunological activity is approximately plus or minus 20%.

The variation in activity that is observed among the different samples is attributed primarily to the test procedure.

The term "reconstituted Beta-1.0" may be applied to a mixture of Beta-1.11 and Beta-1.12 in a predetermined proportion. This so-called reconstituted Beta-1.0 is not the same thing as the leukocyte dialysate Beta-1.0. Beta-1.0, as described above, is a leukocyte dialysate that contains Beta-1.11, Beta-1.12, phenylalanine, and other products, in relative proportion that vary from sample to sample because of the innate variablility of the human immune system. However, reconstituted Beta-1.0 is a mixture of just Beta-1.11 and 1.12 dialysates, in a predetermined proportion.

As used hereinafter, standardized reconstituted Beta-1.0 refers to a mixture of 20 parts of standardized Beta-1.11 and 1 part standardized Beta-1.12. For our purposes, it is appropriate also to standardize the concentration of immunoamplifier to 30 pg/ml of sterile saline.

EXAMPLE 22

Beta-1.0 Repeatability Test

The procedure Example 21 is repeated with five samples of standardized reconstituted Beta-1.0, prepared over a six month interval from available leukocyte sources. It is found that the results of the antigen-induced production of gamma interferon assay vary from sample to sample, so that in comparison with the mean, the maximum to minimum range of immunological activity is approximately plus or minus 20%.

As indicated earlier, an appropriate reconstitution of Beta-1.0 would also include Beta-1.13 in the same proportion as Beta-1.12. (It should be noted that Beta-1.11, 1.12, and 1.13 have approximately equal intrinsic amplifier activity per unit weight.)

Synthetic Tyr-Gly (L-tyrosylglycine, Sigma Chem. Co., St. Louis, Mo.) is advantageously employed as a standard or calibrating agent. It is believed that its intrinsic immunological activity inherently should not vary, as that of endogenous material may, from batch to batch. However, it should be noted that synthetic Tyr-Gly appears to be less potent immunologically than endogenous YG-material. It therefore appears that it is not the same molecular entity or form as the latter. In the previously cited paper, 6 Bio/Technology 810 (1988), a comparison was published of the relative activity of "ZB-4" (purified endogenous Tyr-Gly) and "B-4" (commercial synthetic Tyr-Gly) in inducing the formation of gamma interferon in vitro (see Example 9 of this specification). As shown at Table 3 of the foregoing paper, p. 814, the endogenous Tyr-Gly product was found to be approximately 10 to 20 times more active than synthetic Tyr-Gly.

In addition, the inventor made DH skin tests to compare the activity of Beta-1.0 with purified synthetic Tyr-Gly and Tyr-Gly-Gly. The purpose of the in vivo tests was to ascertain the maximum area of induration resulting from subcutaneous injections of a patient with various dilutions of the three amplifiers. In all cases the maximum induration was achieved at approximately 24 hours after injection. The area of induration for synthetic Tyr-Gly was approximately equal to that for synthetic it is both of the foregoing areas were approximately 60% of the area of induration for the endogenous product Beta-1.0. While DH skin tests are subjective and inherently less quantitatively accurate than in vitro gamma interferon assays, nonetheless, the foregoing DH test results were consistent with the gamma interferon assays and indicated that the synthetic products are less immunologically active than the endogenous products. The result must be attributed to a difference in the synthetic and endogenous products used in these tests.

EXAMPLE 23

Synthetics Repeatability Tests

Five batches of synthetic Tyr-Gly and synthetic Tyr-Gly-Gly are prepared in accordance with the procedure of Example 1, U.S. Pat. No. 4,699,898.

The procedure of Example 21 is repeated with samples from each batch. It is found that the results of the antigen-induced production of gamma interferon assay vary from sample to sample, so that in comparison with the mean, the maximum to minimum range of immunological activity is approximately plus or minus 25%, for both Tyr-Gly and Tyr-Gly-Gly.

It appears that the endogenous standardized products and the synthetic products are approximately equal in repeatability, but the endogenous products are significantly more potent than the synthetic products. However, the synthetic products can be used as calibration products for assaying the endogenous products, by making an appropriate predetermined allowance for the difference in potency (for example, using the activity of 10 pg of synthetic Tyr-Gly as the standard for the activity of 1 pg of endogenous Tyr-Gly, in a gamma interferon assay).

GENERAL CONCLUDING REMARKS

The above described endogenous amplifiers of the immune system are considered to be materials whose natural function is regulation of the immune response, directly with respect to cell-mediated immunity and perhaps indirectly affecting humoral immunity as well. The materials have been prepared with a high degree of purity such that their molecular structure has been more fully characterized than hitherto possible. Furthermore, the materials of this invention have been purified sufficiently to permit their administration to human subjects to produce beneficial effects, without known harmful side effects. Such beneficial effects include immunostimulation of immunodeficient patients, such as victims of AIDS and ARC, and retardation of the normal progression to AIDS from ARC. While not curative of AIDS and ARC, the materials of the invention have substantial therapeutic effects, alleviating certain AIDS/ARC symptoms and reversing or slowing some harmful effects of the diseases. For example, candidiasis has been shown in the above data to be alleviated by this treatment.

The products described above have been shown to increase a person's endogenous production of various modifiers of biological responses that human lymphocytes produce, at least when the person's immune system has not already been so injured as to be beyond the reach of therapy. Such lymphocyte-generated modifiers of biological response have been shown to include the specific lymphokines IL-2 and gamma-interferon.

The foregoing discovery that human leukocyte dialysates contain endogenous amplifier materials, which can be extracted, purified, and administered to patients, is considered significant in several respects. First, it is significant that these materials may be isolated from normal individuals, rather than from specific identified donors, because this permits (and in fact has actually led to) large-scale purification of the materials from pooled sources. Second, the discovery that some endogenous amplifier material contains as intrinsically active components low-M.W. peptide products opens the way to basically chemical, rather than basically biological, preparation of amplifier compositions.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains.

The subject matter claimed is:

1. A purified human leukocyte dialysate, purified of substantially all endotoxin and pyrogen, possessing intrinsic immunoamplifier activity, wherein substantially all of said activity resides in one or more substantially pure materials having M.W.<500.

2. A purified human leukocyte dialysate in accordance with claim 1, wherein said materials consist essentially of pure dipeptide and/or tripeptide materials having Tyr and Gly amino acid residues and containing no extraneous-peptide amino acid residues.

3. The product of claim 2 where said material is a dipeptide having a Tyr-Gly amino acid sequence.

4. The product of claim 2 where said material is a tripeptide having a Tyr-Gly-Gly amino acid sequence.

5. The product of claim 2 where said material contains a mixture of a dipeptide having a Tyr-Gly amino acid sequence and a tripeptide having a Tyr-Gly-Gly amino acid sequence.

6. The product of claim 5 wherein said peptide and tripeptide are present in a ratio of from 25:1 to 10:1.

7. A preparation having a standardized immunoamplifier activity, said preparation comprising a mixture of purified human leukocyte dialysates having intrinsic immunoamplifier activity, said activity residing in substantially pure immunoamplifier materials having M.W.<500, wherein said preparation has been standardized for immunamplifier activity by dilution thereof from a more concentrated preparation of said dialysates until the preparation contains a predetermined per-unit quantity of Tyr-Gly, said preparation having been purified of substantially all endotoxin and pyrogen.

8. The product of claim 7 wherein said immunoamplifier materials are a dipeptide having a Tyr-Gly amino acid sequence and a tripeptide having a Tyr-Gly-Gly amino acid sequence.

9. The product of claim 8 wherein said immunoamplifier materials are (a) said dipeptide and (b) said tripeptide, and wherein (i) said tripeptide represents from 0% to 10% of the total content of said material, and (ii) the remainder of said material consists of said dipeptide.

10. The product of claim 8 wherein 90% to 95% of said immunoamplifier material consists of said dipeptide.

11. The product of claim 8, wherein phenylalanine is also present.

12. The product of claim 11 wherein said phenylalanine is present in an amount of up to approximately ten times the weight of the immunoamplifier material present.

13. The product of claim 8 wherein said dipeptide is present in a concentration of approximately 30 pg/ml of sterile saline.

14. A preparation having a standardized immunoamplifier activity, said preparation comprising a purified human leukocyte dialysate having intrinsic immunoamplifier activity, said activity residing in a first substantially pure immunoamplifier material, said first material having M.W.<500 and being characterized by presence of the amino acid residue Tyr-Gly and no other amino acid groups, wherein said preparation has been standardized for immunoamplifier activity by dilution thereof from a more concentrated preparation of said dialysate until the preparation contains a predetermined per-unit quantity of Tyr-Gly, said preparation having been purified of substantially all endotoxin and pyrogen.

15. A preparation according to claim 14 wherein said preparation also contains a second substantially pure immunoamplifier material, said second material having M.W.<500 and being characterized by presence of the amino acid residue Tyr-Gly-Gly and no other amino acid groups, said second material being present in said preparation in an amount less than 10% of the amount of said first immunoamplifier material present in said preparation.

16. A dialysate in accordance with claim 1 wherein said material is one further characterized as:

(a) containing a Tyr-Gly amino acid residue sequence;
(b) being elutable from an HPLC octadecylsilane column with a solvent system of acetonitrile in aqueous trifluoroacetic acid; and
(c) being associated with a sharp narrow UV 210 nm absorption peak.

17. A dialysate in accordance with claim 16, having no amino acid groups other than said Tyr-Gly amino acid residue sequence and having M.W.<300.

18. A dialysate in accordance with claim 16, wherein said dialysate is elutable from said solvent system at an acetonitrile concentration of less than 20%.

* * * * *